(12) United States Patent
Fukugaki et al.

(10) Patent No.: US 8,877,128 B2
(45) Date of Patent: Nov. 4, 2014

(54) AUTOMATED SAMPLE TESTING SYSTEM

(75) Inventors: Tatsuya Fukugaki, Hitachinaka (JP); Masaaki Hanawa, Hitachinaka (JP); Hiroshi Ohga, Hitachiomiya (JP)

(73) Assignee: Hitachi High-Technologies Corporation, Tokyo (JP)

( * ) Notice: Subject to any disclaimer, the term of this patent is extended or adjusted under 35 U.S.C. 154(b) by 152 days.

(21) Appl. No.: 13/389,942

(22) PCT Filed: Sep. 8, 2010

(86) PCT No.: PCT/JP2010/065435
§ 371 (c)(1),
(2), (4) Date: Mar. 9, 2012

(87) PCT Pub. No.: WO2011/040197
PCT Pub. Date: Apr. 7, 2011

(65) Prior Publication Data
US 2012/0177547 A1    Jul. 12, 2012

(30) Foreign Application Priority Data

Sep. 30, 2009    (JP) ................................. 2009-225927

(51) Int. Cl.
*G01N 35/00* (2006.01)
*G01N 35/02* (2006.01)
*G01N 35/04* (2006.01)

(52) U.S. Cl.
CPC ...... *G01N 35/026* (2013.01); *G01N 2035/0467* (2013.01); *G01N 2035/046* (2013.01); *G01N 2035/047* (2013.01); *G01N 2035/0427* (2013.01)
USPC ................. 422/65; 422/62; 422/63; 422/624; 422/547; 414/222.11; 414/507; 414/595; 198/346.2; 198/346.3; 198/347.4; 198/370.03; 198/406; 198/463.3

(58) Field of Classification Search
None
See application file for complete search history.

(56) References Cited

U.S. PATENT DOCUMENTS 5,941,366 A * 8/1999 Quinlan et al. ............ 198/465.1
5,966,309 A * 10/1999 O'Bryan et al. ............. 700/225

(Continued)

FOREIGN PATENT DOCUMENTS

| JP | 04-082681 A | 3/1992 |
| JP | 04-204159 A | 7/1992 |

(Continued)

OTHER PUBLICATIONS

Machine Translation of JP 07234228 A.*
Machine Translation of JP 05116735 A.*

*Primary Examiner* — Jill Warden
*Assistant Examiner* — Benjamin Whatley
(74) *Attorney, Agent, or Firm* — Mattingly & Malur, PC

(57) ABSTRACT

An empty rack transport line is arranged at a lower stage and independent of a main transport line, a fast emergency line and a reverse line. In a rack stocker, an inclined transport line connects the empty rack transport line to the rack stocker. The rack stocker is arranged between a storage module and a loading module. The rack stocker is capable of continuously supplying and collecting empty racks, while transport lines do not cross each other. It is, therefore, possible to continuously supply and collect empty racks in a simple configuration, without an increase in the system size, an intersection of transport lines and a reduction in processing capability. In addition, it is possible to provide an automated sample testing system that is highly extendable for various facility sizes.

4 Claims, 3 Drawing Sheets

(56) References Cited

U.S. PATENT DOCUMENTS

| | | | |
|---|---|---|---|
| 6,202,829 B1* | 3/2001 | van Dyke et al. | 198/465.2 |
| 6,557,724 B1* | 5/2003 | LeCroy et al. | 221/76 |
| 2002/0159865 A1* | 10/2002 | Konstant | 414/267 |
| 2004/0141882 A1* | 7/2004 | Mimura et al. | 422/63 |
| 2007/0202011 A1* | 8/2007 | Nogawa et al. | 422/65 |
| 2008/0008624 A1* | 1/2008 | Veiner et al. | 422/63 |
| 2011/0160899 A1* | 6/2011 | Tatsutani et al. | 700/218 |
| 2013/0197690 A1* | 8/2013 | Suzuki et al. | 700/216 |

FOREIGN PATENT DOCUMENTS

| | | | |
|---|---|---|---|
| JP | 05-116735 A | | 5/1993 |
| JP | 05116735 A | * | 5/1993 |
| JP | 07-234228 A | | 9/1995 |
| JP | 07234228 A | * | 9/1995 |
| JP | 08-122337 A | | 5/1996 |
| JP | 3618067 B2 | | 11/2004 |
| JP | 2005-156196 A | | 6/2005 |
| JP | 2007-309675 A | | 11/2007 |

* cited by examiner

AUTOMATED SAMPLE TESTING SYSTEM

TECHNICAL FIELD

The present invention relates to an automated sample testing system, and more particularly to an automated sample testing system that performs a clinical test on a large number of patient's samples.

BACKGROUND ART

Reductions in examination work in the medical field have recently proceeded by introducing diverse automated devices. For testing in a hospital, the samples of inpatients and outpatients are collected from several sections of the hospital and collectively processed in a examination room. Test items for each sample are sent from doctors to the examination room by use of an online information processing system. Test results are then reported online from the examination room to the doctors. For many of test items on blood or urine, pretreatment for testing needs to be performed such as centrifugal processing, unplugging, dispensing, and the like. It takes much time for engagement in such pretreatment work and increases the total hours required to perform testing.

Next, the flow of a process to be performed by a general automated sample testing system is described. A test tube that holds a body fluid such as blood collected from a patient is held by a sample rack. The sample rack holding the test tube is loaded into the general automated sample testing system. Barcode information of the loaded sample is read in the system so that the sample type is recognized. As described above, the centrifugal process, unplugging, dispensing, and the like are performed as the pretreatment for the test process. The contents of the pretreatment vary depending on the sample type, for example, for a urine test, the centrifugal process does not need to be performed. A sample type that needs to be subjected to the centrifugal separation is a sample on which the unplugging and dispensing are performed after centrifugal separation. The dispensing process is a process in which a child sample is generated from a parent sample. For example, dispensed child samples can be simultaneously transported to multiple analyzers that are connected to the system online. In addition, the dispensing process transports a child sample with the same barcode as that of a parent sample attached to a sorting tray for testing in an analyzer which is not connected to the system online. A sample that is completed with all processes is stored in a storage module.

The automated sample testing system is introduced in a relatively large facility where hundreds to thousands of samples are processed in a day. In such large facility, many samples are collected from one patient for multiple testing such as a biochemical test, an immunological test, a solidification test, and a hematological test. Therefore, the number of sample racks for the hundreds to thousands patients are needed for loading into the automated sample testing system, and accordingly, a space for installing and storing those sample racks is required.

As described in Patent Document 1, for a loading device that loads a sample rack into the conventional automated sample testing system, a method for setting a large number of sample racks in advance into the device in order to perform a process based on the sample type is known, for example. Further, Patent Document 2 describes that a certain number of sample racks are set on trays that are arranged in a sample rack supply unit and a rack collecting unit. The sample rack supply unit and the rack collecting unit are arranged at multiple stages so that sample racks are supplied and collected by an elevator mechanism that is driven and moves up and down. This, therefore, reduces the area for setting the sample racks. Patent Document 3 describes a method that a loading device is connected to an endless transport line and a sample rack is used repeatedly.

PRIOR ART LITERATURE

Patent Documents

Patent Document 1: Japanese Patent No. 3618067
Patent Document 2: JP-2007-309675-A
Patent Document 3: JP-8-122337-A

SUMMARY OF THE INVENTION

Problems to be Solved by the Invention

In the methods described in Patent Documents 1 and 2, in order to process a large number of samples, it is necessary to prepare the sample racks for a large number of samples to be tested, therefore it is inevitable that the system becomes large and complicated. Further, an operator is required to replenish a large number of sample racks before use of the system.

In Patent Document 3, not a large number of sample racks are necessary since the transport line for the sample racks loops in a system so as to reuse the sample racks. However, empty sample racks and sample racks holding samples pass through the sample transport line, thereby congesting the transport line, and making it difficult to build a system capable of processing a sample at high speed. In addition, since it is necessary to discriminate a sample rack holding a sample from an empty sample rack, control of the transport becomes inevitably complicated. In order to avoid this, a method is conceivable that provides a transport line for sample racks holding samples and dedicated line for an empty sample rack separately. In this case, the processing speed is lowered since the transport lines cross each other.

Meanwhile, yet another method is considered that a large number of empty sample racks are supplied into and collected from one space where a large number of empty sample racks are stored. Nevertheless, a difficulty remains in storing optimal number of sample racks for the size of a facility. This could excessively enlarge the system for the size of a facility.

It is, therefore, an object of the present invention to provide an automated sample testing system that is suitable for a high-speed processing with high extendibility and can be readily built without increasing the system size, reducing processing speed due to an intersection of transport lines, and complicating transport control.

Means for Solving the Problem

In order to solve the aforementioned problems, an automated sample testing system according to claim 1 of the present invention includes: a main transport line for transporting a sample rack holding a sample; a plurality of sample processing units that are arranged along the main transport line; a rack stocker that supplies and collects a sample rack to be transported to the main transport line; an empty rack transport line that is provided for an empty rack and extends in parallel to the main transport line; and an inclined transport line for connecting the rack stocker to the empty rack transport line, wherein the empty rack transport line is arranged at a lower stage than the main transport line.

In addition, according to claim 2 of the present invention, in the automated sample testing system, the empty rack transport line is a dedicated line that is independent of the main transport line, and the empty rack transport line and the main transport line are parallel to each other and constituted by a forward line, a reverse line and a branched line for connecting the forward line to the reverse line, the forward line and the reverse line extend in parallel to each other.

In addition, according to claim 3 of the present invention, in the automated sample testing system, the transport line for connecting the rack stocker to the empty rack transport line is perpendicular to the main transport line.

In addition, an automated sample testing system according to claim 4 of the present invention includes: a main transport line for transporting a sample rack holding a sample; a plurality of sample processing units that are arranged along the main transport line; a rack stocker for supplying and collecting a sample rack to be transported to the main transport line; a loading module for loading the sample into the system; and a storage module for storing the sample completed with processing, wherein the storage module, the rack stocker and the loading module are arranged in this order in a direction in which the sample rack is transported so that the storage module and the rack stocker are adjacent to each other and the rack stocker and the loading module are adjacent to each other.

Effects of the Invention

As described above, according to the present invention, it is possible to provide an automated sample testing system with a simple configuration without increasing the size of the system, complicating the system, and an intersection of transport lines. The present invention further provides the automated sample testing system that can supply and collect empty racks in succession and is highly extendable corresponding to the size of a facility without reducing a processing capability.

MODE FOR CARRYING OUT THE INVENTION

Figure 1:
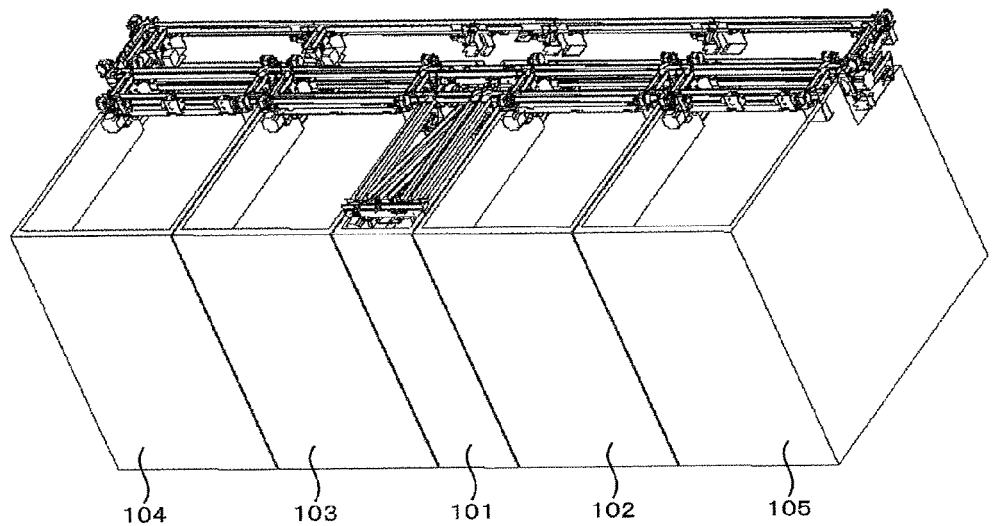
FIG. 1 is a perspective view of the entire configuration of a system including a transport line unit for a sample rack according to the present invention.
Figure 2:
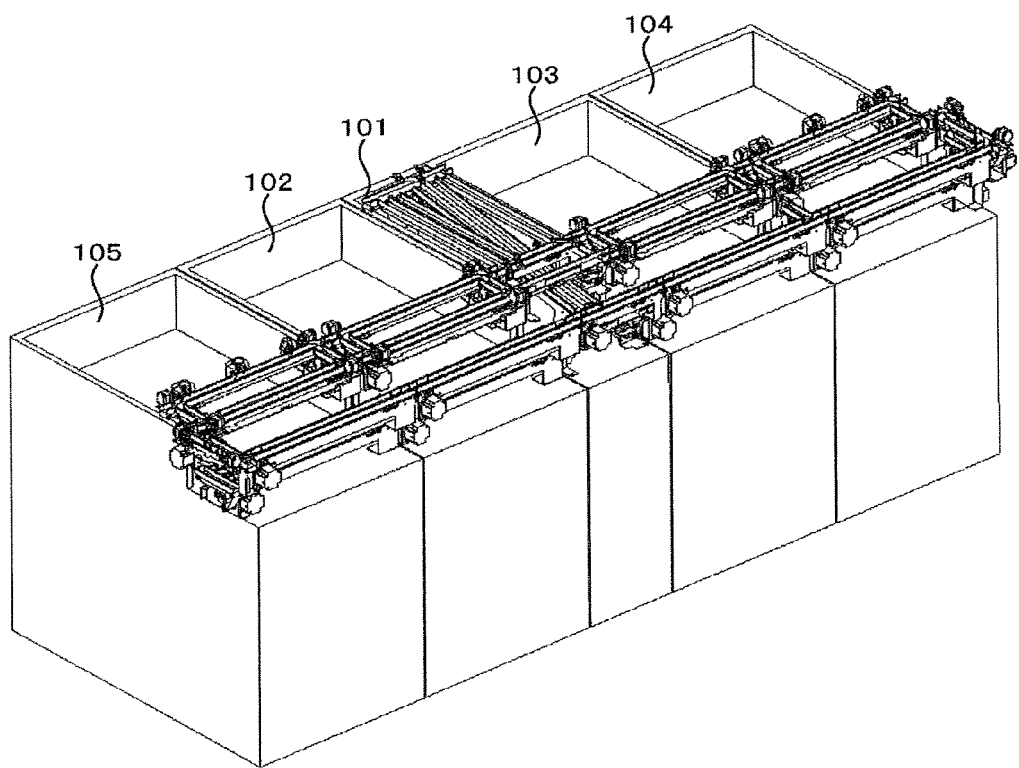
FIG. 2 is a perspective view of the entire configuration of the system according to the present invention when the system is viewed from a back side of the system.

FIG. 1 is a perspective view of the entire configuration of a system including a transport line unit for a sample rack according to the present invention. FIG. 2 is a perspective view of the entire configuration of the system according to the present invention when the system is viewed from a back side of the system. In this embodiment, only five processing modules are described, however, ten or more processing modules may be connected in a large facility.

Figure 3:
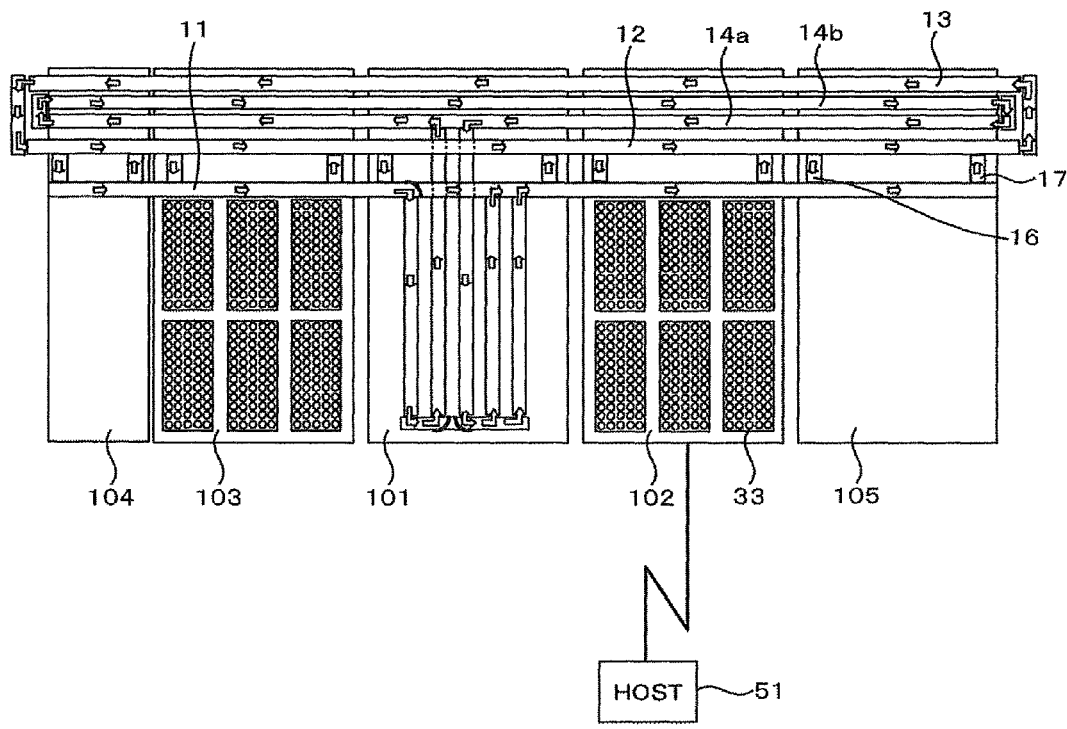
FIG. 3 is a schematic diagram illustrating the transport line unit for a sample rack which is included in the system according to the present invention.

FIG. 3 is a schematic diagram illustrating the transport line unit for a sample rack which is included in the system. Sample racks 31, uniquely attached with the ID numbers, have a structure that enables the sample rack 31 to be transported on a line, while a sample 32 contains a body fluid such as blood collected from a patient, and the sample 32 is held upright by the sample rack 31. The sample racks 31 are transported between the processing modules on a plurality of transport lines that are used for respective purposes. Next, the flow of a sample within the system is described.

A tray 33 capable of holding 50 to 100 samples 32 is mounted on a loading module 102. In the loading module 102, the samples 32 placed on the tray 33 are loaded on the sample racks 31 by a test tube chuck mechanism (not illustrated). The sample racks 31 are stored in the vicinity of an output port of a rack stocker 101. The sample racks 31 are sequentially transported to the loading module 102 in response to a request from the loading module 102. After the samples 32 are loaded on the sample racks 31, barcode information attached to the samples 32 are read in the loading module 102. The read barcode information is transmitted to a host computer 51. Then, information concerning the type of the interested samples registered in the host computer 51 is transmitted to the system. The system determines, based on type information the system received from the host computer 51, which processing modules the samples 32 stop by or which processing modules the samples 32 skip. The samples 32 loaded on the sample racks 31 are transported to the processing modules on the basis of the information, and the samples 32 completed with all the processing are finally transported to a storage module 103. The sample 32 removed from the sample rack 31 by the test tube chuck mechanism (not illustrated) are stored in the tray 33. Then the empty sample rack 31 from which the sample 32 has been removed is transported to the rack stocker 101.

A main transport line 11 is a line for transporting the samples 32 loaded in the system to the processing modules. A fast emergency line 12 is a line for an emergent sample to overtake another sample. The line 12 also bypasses those samples without the need to stop by any processing modules (e.g. a sample that skips centrifugal processing) by use of branched lines 16, 17 which are disposed on each of the modules. A reverse line 13 is a transport line for the samples 32 to loop in the system. For example, when a sample needs to take a re-examination such as re-dispensing, the sample loops in the system by use of the reverse line 13. Empty rack transport lines 14a and 14b are provided in parallel to the main transport line 11, and have the equal length to the main transport line 11. The empty rack transport lines 14a and 14b are arranged between the main transport line 11 and the reverse line 13. The lengths of the empty rack transport lines 14a and 14b are set equal to the lengths of the main transport line 11 and the reverse line 13 in order for the system to be readily extendable (addition/removing of processing modules). Specifically, empty racks are provided so that the optimal number of the empty racks for the system size is provided. The number of empty racks that are necessary for system operation is equal to the number of racks 31 with which the lines are filled. In other words, any racks other than the racks with which the lines are filled is unnecessary. When the fast emergency line 12 is basically defined so that the sample racks are not stopped and only pass through the processing modules, the total length of the main transport line 11 and the reverse line 13 is equal to the total length of the empty rack transport lines 14a and 14b, and empty racks necessary for the system can be stored in the empty rack transport lines 14a and 14b. Thus, empty racks can be always provided so that the optimal number of the empty racks for the size of the system is provided.

In addition, the empty rack transport line 14a transports, in a direction opposite to a transport direction of the main transport line, empty racks continuously transported from the storage module 103 in order to efficiently collect the empty racks, without the empty rack transportation line 14a crosses another line in the rack stocker 101. In the same manner as the empty rack transport line 14a, the empty rack transport line 14b transports empty racks in a direction opposite to a transport direction of the reverse line 13.

Figure 4:
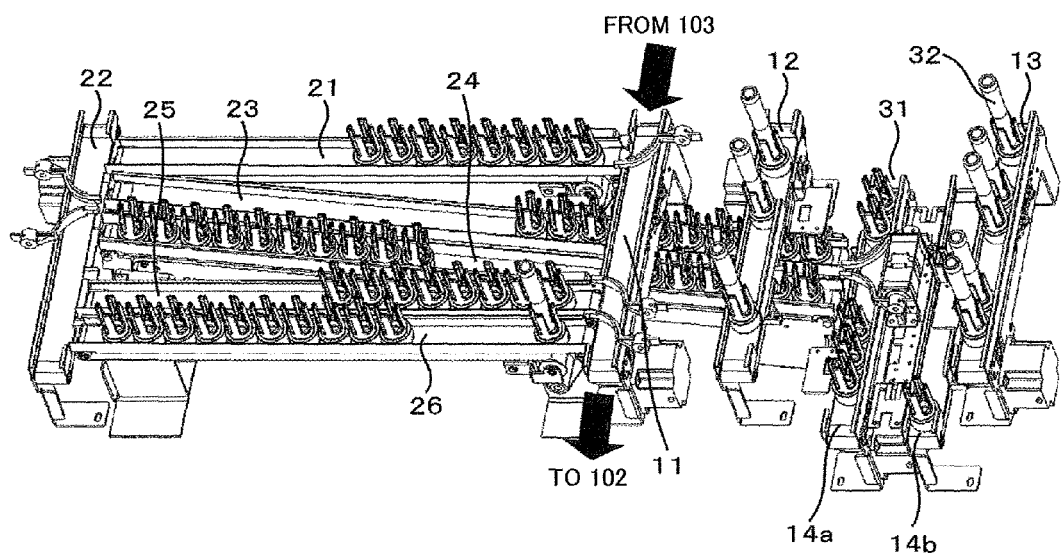
FIG. 4 is a perspective view of only the transport line unit included in a rack stocker according to the present invention.

FIG. 4 is a perspective view of only the transport line unit included in the rack stocker 101. The flow of a rack within the rack stocker 101 is described below with reference to FIG. 4. An empty rack from which a sample is removed in the storage module 103 passes through the main transport line 11 and then transported to a line 21 and a line 22. A plurality of empty racks are always held in a supply line 25. An empty rack is transported in response to a transport request from the loading module 102. When the supply line 25 is filled with empty racks, an empty rack that is transported from the storage module 103 passes through an inclined collection line 23 and is transported to the empty rack transport line 14a. Similarly, when an empty rack is not transported from the storage module 103 and the number of racks remaining on the supply line 25 is small, an empty rack is transported from the empty rack transport line 14a through an inclined supply line 24 and the line 22 to the supply line 25. As illustrated in FIG. 4, the empty rack transport lines 14a and 14b are located lower than the main transport line 11, the fast emergency line 12 and the reverse line 13. Since the empty rack transport lines 14a and 14b are connected to the main transport line 11, the fast emergency line 12 and the reverse line 13 by the inclined collection line 23 and the inclined supply line 24, the transport lines do not cross each other, and empty racks can be efficiently supplied and collected in a simple configuration, compared with an elevator scheme and a robot hand scheme.

In the present embodiment, the straight inclined lines are illustrated. The transport lines that connect the rack stocker arranged at an upper stage to the empty rack transport lines arranged at a lower stage may be of any type as long as the transport lines connect the upper stage to the lower stage. The transport lines that connect the rack stocker to the empty rack transport lines may be spiral transport lines so that a buffer amount of empty racks is increased.

A manual loading line 26 uses a characteristic in which an empty rack is always stocked in the rack stocker 101. A sample 32 is manually inserted from the manual loading line 26 directly into a sample rack 31. When a start switch (not illustrated) is pressed, the manual loading line 26 can transport the sample rack 31 to the loading module 102. The manual loading line 26 is controlled so that the number of empty racks is always a certain number in the same manner as that of the supply line 25. When the number of empty racks becomes lower than the certain number, an empty rack is supplied from an empty rack supply line.

Figure 5:
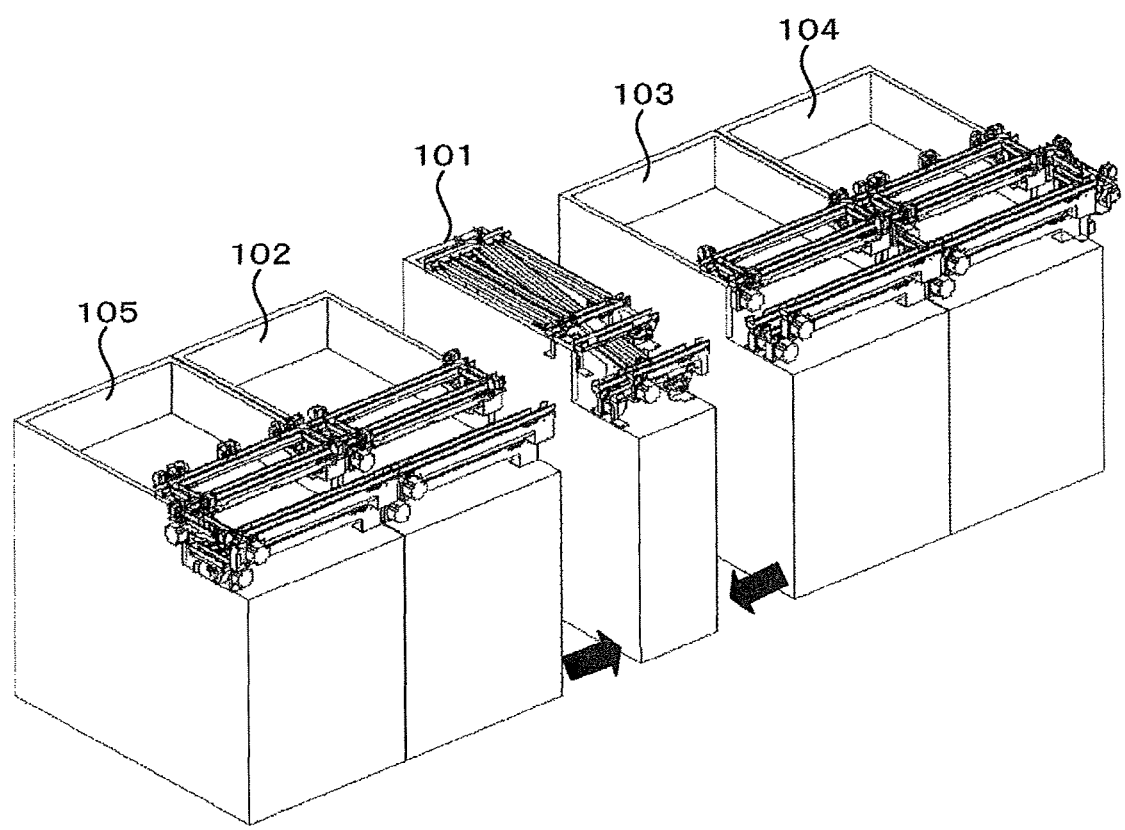
FIG. 5 is a perspective view of a combination of processing modules according to the present invention.

FIG. 5 is a perspective view of a combination of the processing modules. In order to significantly improve the expendability of the system (addition/removing of processing modules), interfaces of the processing modules are standardized and a transport line platform within the system is used as a common platform. Thus, the processing modules can be arbitrarily and readily combined corresponding to the facility. It is preferable that the storage module 103, the rack stocker 101 and the loading module 102 be arranged in this order in a traveling direction of racks in order to continuously supply and collect empty racks. In addition, it is preferable that the processing modules be continuously combined so that time periods for transport between the processing modules are minimized and the total process time is short. Furthermore, it is preferable that the transport lines be arranged on the back side of the system so that an operator can easily access to the front side of the system in order to place a sample and set a consumable supply.

DESCRIPTION OF REFERENCE NUMERALS

11 Main transport line
12 Fast emergency line
13 Reverse line
14a, 14b Empty rack transport line
16, 17 Branched line
21, 22 Transport line
23 Inclined collection line
24 Inclined supply line
25 Supply line
26 Manual loading line
31 Sample rack
32 Sample
33 Tray
51 Host computer
101 Rack stocker
102 Loading module
103 Storage module
104, 105 Processing module

The invention claimed is:

1. An automated sample testing system comprising: a main transport line for transporting a sample rack holding at least one sample; a plurality of processing units that are arranged along the main transport line; an empty rack transport line for transporting an empty sample rack and which extends in parallel to the main transport line; a straight inclined collection line for transporting the empty sample rack from the main transport line to the empty rack transport line; a straight inclined supply line for transporting the empty sample rack from the empty rack transport line to the main transport line; a first transport line for transporting the empty sample rack from the main transport line to the straight inclined collection line and connected therewith; and a second transport line for transporting the empty sample rack from the straight inclined supply line to the main transport line and connected therewith, wherein the empty rack transport line is arranged at a lower stage than the main transport line.

2. The automated sample testing system according to claim 1, wherein the empty rack transport line is a dedicated line that is independent of the main transport line, and wherein the empty rack transport line includes a forward line and a reverse line which extend in parallel to each other.

3. The automated sample testing system according to claim 1, further comprising: a main transport line for transporting a sample rack holding at least one sample; a first sample processing unit that is arranged along the main transport line; a rack stocker that is arranged along the main transport line and includes the straight inclined collection line and the straight inclined supply line; a loading module that is arranged along the main transport line and loads the sample onto the main transport line; and a storage module that is arranged along the main transport line and stores the sample which has completed processing, wherein one of the processing units, the storage module, the rack stocker, the loading module and another of the processing units are arranged in this order so that the storage module is adjacent to the one of the processing units and the rack stocker, and the loading module is adjacent to the rack stocker and the another of the processing units.

4. The automated sample testing system according to claim 1, wherein the first transport line, the second transport line, the straight inclined collection line and the straight inclined supply line are perpendicular to the main transport line.

* * * * *